United States Patent
Govari et al.

(10) Patent No.: US 7,613,497 B2
(45) Date of Patent: Nov. 3, 2009

(54) ENERGY TRANSFER AMPLIFICATION FOR INTRABODY DEVICES

(75) Inventors: Assaf Govari, Haifa (IL); Michael Levin, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 941 days.

(21) Appl. No.: 10/629,660

(22) Filed: Jul. 29, 2003

(65) Prior Publication Data
US 2005/0027192 A1 Feb. 3, 2005

(51) Int. Cl.
*A61B 5/05* (2006.01)
(52) U.S. Cl. .................... 600/424; 607/61; 600/407; 600/409; 600/422; 600/423
(58) Field of Classification Search .......... 600/407–409, 600/61, 485, 424, 422, 423
See application file for complete search history.

(56) References Cited

U.S. PATENT DOCUMENTS

| | | | |
|---|---|---|---|
| 4,741,339 A | 5/1988 | Harrison et al. | |
| 5,057,095 A | 10/1991 | Fabian | |
| 5,325,873 A | 7/1994 | Hirschi et al. | |
| 5,391,199 A | 2/1995 | Ben-Haim | |
| 5,443,489 A | 8/1995 | Ben-Haim | |
| 5,755,748 A * | 5/1998 | Borza | 607/61 |
| 6,026,818 A | 2/2000 | Blair et al. | |
| 6,053,873 A | 4/2000 | Govari et al. | |
| 6,076,007 A | 6/2000 | England et al. | |
| 6,172,499 B1 | 1/2001 | Ashe | |
| 6,198,963 B1 | 3/2001 | Haim et al. | |
| 6,206,835 B1 * | 3/2001 | Spillman et al. | 600/485 |
| 6,216,026 B1 * | 4/2001 | Kuhn et al. | 600/409 |
| 6,226,542 B1 | 5/2001 | Reisfeld | |
| 6,239,724 B1 | 5/2001 | Doron et al. | |
| 6,261,247 B1 | 7/2001 | Ishikawa et al. | |
| 6,285,898 B1 | 9/2001 | Ben-Haim | |
| 6,301,496 B1 | 10/2001 | Reisfeld | |
| 6,366,817 B1 * | 4/2002 | Kung | 607/61 |

(Continued)

FOREIGN PATENT DOCUMENTS

WO     WO 96/05768    *   2/1996

(Continued)

OTHER PUBLICATIONS

U.S. Appl. No. 08/793,371, Biosense Webster, Inc., issued US 6,690,963.

(Continued)

*Primary Examiner*—Brian Casler
*Assistant Examiner*—John F Ramirez
(74) *Attorney, Agent, or Firm*—Louis J. Capezzuto

(57) ABSTRACT

Apparatus for driving current in a power circuit of a medical device inserted into a body of a subject includes a power transmitter, which is adapted to generate, in a vicinity of the body, an electromagnetic field having a predetermined frequency capable of inductively driving the current in the power circuit. A passive energy transfer amplifier, having a resonant response at the frequency of the electromagnetic field is placed in proximity to the medical device so as to enhance the current driven in the power circuit by the electromagnetic field.

19 Claims, 4 Drawing Sheets

U.S. PATENT DOCUMENTS

| | | |
|---|---|---|
| 6,368,285 B1 | 4/2002 | Osadchy et al. |
| 6,385,476 B1 | 5/2002 | Osadchy et al. |
| 6,400,981 B1 | 6/2002 | Govari |
| 6,430,444 B1 | 8/2002 | Borza |
| 6,484,118 B1 | 11/2002 | Govari |
| 6,503,249 B1 | 1/2003 | Krause |
| 7,001,346 B2 * | 2/2006 | White .................. 600/587 |

FOREIGN PATENT DOCUMENTS

| | | |
|---|---|---|
| WO | WO 96/05768 A1 | 2/1996 |
| WO | WO 03/030991 A1 | 4/2003 |

OTHER PUBLICATIONS

Pending U.S. Appl. No. 09/506,766, Biosense Webster, Inc.
Pending U.S. Appl. No. 10/029,473, Biosense Webster, Inc.

* cited by examiner

ENERGY TRANSFER AMPLIFICATION FOR INTRABODY DEVICES

FIELD OF THE INVENTION

The present invention relates generally to position sensing systems, and specifically to methods and devices for enhancing the transfer of energy to wireless position sensing systems inserted into the human body.

BACKGROUND OF THE INVENTION

Many surgical, diagnostic, therapeutic and prophylactic medical procedures require the placement of objects such as sensors, implants, tubes, catheters and treatment devices within the body. These procedures cover a large spectrum including, for example: a) placement of tubes to facilitate the delivery of drugs, nutrition or other fluids into a patient's circulatory or digestive system, b) placement of tubes to facilitate respiration of a patient, c) placement of tubes to facilitate removal of gastrointestinal tract contents for analysis and/or treatment, d) insertion of probes or surgical devices for diagnostic or therapeutic treatments, and e) placement of orthopedic devices such as artificial hips and knees.

In some instances, placement of a device is for a limited time, such as during surgery or catheterization. In other situations, such as with feeding tubes or orthopedic implants, the devices are to be used for long-term treatment. It is beneficial to provide real-time information for accurately determining the location and orientation of objects both during and after implantation within a patient's body, preferably without using X-ray imaging.

Noninvasive techniques for determining the location and orientation of implanted devices are often preferred, as such techniques are generally more comfortable for the patient and easier to perform. Field sensors, such as Hall effect devices, coils or antennae, have been included in medical devices to allow for noninvasive monitoring of the position of the devices.

PCT Patent Publication WO 96/05768 to Ben-Haim et al. and corresponding U.S. patent application Ser. No. 08/793,371, which are assigned to the assignee of the present patent application and which are incorporated herein by reference, describe a locating system for determining the location and orientation of an invasive medical instrument, whereby an externally-applied RF field induces a current in three coils located within the invasive medical instrument. Wires or some other form of physical leads are used to carry this induced signal from the catheter to a signal processor in the extrabody space. The processor analyzes the signal so as to calculate the location and orientation of the invasive medical instrument.

In many applications, a wireless passive emitter, or "tag," is affixed to a device that is inserted into the body. Such a tag contains no internal power source, but is rather actuated by an external energy field, typically applied from outside the body. The tag then emits electromagnetic energy, which is detected by antennas or other sensors outside the body. The detected signals are generally used simply to ascertain the presence of the tag within a given region (such as the abdominal cavity), although some tags may also be used to determine position coordinates. Some passive tags receive and re-emit electromagnetic radiation, typically with a frequency and/or phase shift.

For example, U.S. Pat. No. 6,026,818 to Blair et al., whose disclosure is incorporated herein by reference, describes a method and device for the detection of unwanted objects in surgical sites, based on a medically-inert detection tag which is affixed to objects such as medical sponges or other items used in body cavities during surgery. The detection tag contains a single signal emitter, such as a miniature ferrite rod and coil and capacitor element embedded therein. Alternatively, the tag includes a flexible thread composed of a single loop wire and capacitor element. A detection device is utilized to locate the tag by pulsed emission of a wide-band transmission signal. The tag resonates with a radiated signal, in response to the wide-band transmission, at its own single non-predetermined frequency, within the wide-band range. The return signals build up in intensity at a single (though not pre-defined) detectable frequency over ambient noise, so as to provide recognizable detection signals.

U.S. Pat. No. 5,057,095 to Fabian, whose disclosure is incorporated herein by reference, describes apparatus for detecting a surgical implement in human or animal tissue, comprising a detector that is responsive to the presence, within an interrogation zone, of a surgical implement to which a marker is secured. The marker is adapted to produce identifying signal characteristics within a frequency band generated in the interrogation zone. Variations in the phase and or direction of the interrogating field and changes in the electromagnetic coupling between markers and receiver are intended to optimize coupling therebetween.

U.S. Pat. No. 6,076,007 to England et al., whose disclosure is incorporated herein by reference, describes a method for determining the position and orientation of a surgical device within a human body. In one application, a catheter or prosthesis is characterized in that it carries, at a predetermined location, a tag formed of a high permeability, low coercivity magnetic material. The position of the tag (and hence of the surgical device) is sensed by remotely detecting its magnetic response to an interrogating signal.

U.S. Pat. No. 5,325,873 to Hirschi et al., whose disclosure is incorporated herein by reference, describes a system to verify the location of a tube or other object inserted into the body. It incorporates a resonant electrical circuit attached to the object which resonates upon stimulation by a hand-held RF transmitter/receiver external to the body. The electromagnetic field generated due to resonance of the circuit is detected by the hand-held device, which subsequently turns on a series of LEDs to indicate to the user the direction to the target. An additional visual display indicates when the transmitter/receiver is directly above the object.

Passive sensors and transponders, fixed to implanted devices, can also be used for conveying other diagnostic information to receivers outside the body. For example, U.S. Pat. No. 6,053,873 to Govari et al., whose disclosure is incorporated herein by reference, describes a stent adapted for measuring a fluid flow in the body of a subject. The stent contains a coil, which receives energy from an electromagnetic field irradiating the body so as to power a transmitter for transmitting a pressure-dependent signal to a receiver outside the body.

As another example, U.S. Pat. No. 6,206,835 to Spillman et al., whose disclosure is incorporated herein by reference, describes an implant device that includes an integral, electrically-passive sensing circuit, communicating with an external interrogation circuit. The sensing circuit includes an inductive element and has a frequency-dependent variable impedance loading effect on the interrogation circuit, varying in relation to the sensed parameter.

U.S. Pat. Nos. 5,391,199 and 5,443,489 to Ben-Haim, whose disclosures are incorporated herein by reference, describe systems wherein the coordinates of an intrabody probe are determined using one or more field sensors, such as a Hall effect device, coils, or other antennae carried on the probe. Such systems are used for generating three-dimensional location information regarding a medical probe or catheter. Preferably, a sensor coil is placed in the catheter and generates signals in response to externally-applied electromagnetic fields. The electromagnetic fields are generated by three radiator coils, fixed to an external reference frame in known, mutually-spaced locations. The amplitudes of the signals generated in response to each of the radiator coil fields are detected and used to compute the location of the sensor coil. Each radiator coil is preferably driven by driver circuitry to generate a field at a known frequency, distinct from that of other radiator coils, so that the signals generated by the sensor coil may be separated by frequency into components corresponding to the different radiator coils.

U.S. Pat. No. 6,198,963 to Ben-Haim et al., whose disclosure is incorporated herein by reference, describes apparatus for confirmation of intrabody tube location. The initial location of the object is determined as a reference point, and subsequent measurements are made to determine whether the object has remained in its initial position. Measurements are based upon one or more signals transmitted to and/or from a sensor fixed to the body of the object whose location is being determined. The signal could be ultrasound waves, ultraviolet waves, radio frequency (RF) waves, or static or rotating electromagnetic fields.

Other devices comprise multiple transducers which each perform specific tasks. For example, U.S. Pat. No. 6,239,724 to Doron et al., which is incorporated herein by reference, describes an implantable telemetry device that contains one transducer for converting a power signal from outside the body into electrical power for the device, a second transducer for receiving a position field signal form outside the body, and a third transducer for transmitting a signal to a site outside the body.

U.S. Pat. No. 6,172,499 to Ashe, whose disclosure is incorporated herein by reference, describes a device for measuring the location and orientation in the six degrees of freedom of a receiving antenna with respect to a transmitting antenna utilizing multiple-frequency AC magnetic signals. The transmitting component consists of two or more transmitting antennae of known location and orientation relative to one another. The transmitting antennae are driven simultaneously by AC excitation, with each antenna occupying one or more unique positions in the frequency spectrum. The receiving antennae measure the transmitted AC magnetic field plus distortions caused by conductive metals. A computer then extracts the distortion component and removes it from the received signals, providing the correct position and orientation output.

U.S. Pat. No. 6,261,247 to Ishikawa et al., which is incorporated herein by reference, describes an implantable position sensing system comprising a plurality of spherical semiconductors, which are capable of determining their relative positions and communicating this information among each other and to an external processing unit. Radio frequency signals are used for communication and to power the implanted spherical semiconductors.

Current intrabody radio frequency powered position sensors are limited in the amount of power they can receive, due to their typically small size, as induced current varies with cross-sectional area of the receiving coil. Additional power would be desirable, e.g., so that additional computations can be performed by the sensor and/or to increase the strength of the signal transmitted by the sensor.

SUMMARY OF THE INVENTION

It is an object of some aspects of the present invention to provide improved apparatus and methods for wirelessly transmitting power to an intrabody object.

It is a further object of some aspects of the present invention to provide improved apparatus and methods for real-time determination of the location and orientation of intrabody objects.

It is yet a further object of some aspects of the present invention to provide improved position measurement apparatus and methods based on radio frequency electromagnetic signals.

In preferred embodiments of the present invention, energy transfer from an external radio frequency (RF) power transmitter to a wireless intrabody medical device is enhanced by a passive energy transfer amplifier. The amplifier is positioned in proximity to the wireless device so as to enhance inductive driving of a power coil in the device by the external driver. Typically, the energy transfer amplifier comprises an amplification coil with a capacitance chosen so as to define a resonant circuit with a desired resonant frequency. The external RF power transmitter transmits a RF signal at the resonant frequency, which drives a current in the amplification coil of the energy transfer amplifier. The amplification coil preferably has a characteristic diameter substantially larger than that of the power coil. Therefore, the amplification coil re-radiates the RF signal with enhanced local field strength, and thus induces a greater current in the power coil of the wireless medical device than would be provided by the external RF driver alone.

The term "passive," as used in the context of the present patent application and in the claims, refers to electrical units that do not comprise an active power source, such as a battery, and are not wired to such a power source. In the embodiments described herein, such passive units have the advantages of reduced size and essentially unlimited useful life. Thus, in some embodiments of the present invention, passive energy transfer amplifiers are implanted in a patient's body in proximity to other wireless devices. In other embodiments, passive energy transfer amplifiers may be placed on or adjacent to the patient's body, in order to boost the RF power transferred to a wireless device inside the body. These embodiments enable the system operator (such as a surgeon) to place the bulky RF power transmitter, along with its associated wiring, relatively far from the site of the wireless device within the body, so that the transmitter is less likely to interfere with a medical or surgical procedure using the wireless device.

In some preferred embodiments of the present invention, the medical device comprises one or more wireless position sensors, which are used to determine the location and/or orientation of the intrabody medical device. In a preferred embodiment, the medical device comprises a hip joint implant, including a femur head and an acetabulum. A signal processor, typically external to the patient, is adapted to determine a distance between the femur head and the acetabulum responsive to the output signals from the position sensors. Preferably, the energy transfer amplifier is implanted in the acetabulum, in close proximity to the position sensors, so as to improve the wireless transfer of energy to the position sensors. Since the energy transfer amplifier is completely enclosed by the implanted acetabulum, no additional surgical procedure is necessary to implant the apparatus. Moreover, since the energy transfer amplifier is isolated from bodily tissues, biocompatibility issues are generally minimal. Alternatively, the energy transfer amplifier is implanted in body tissue adjacent to the hip joint implant. Further alternatively, the energy transfer amplifier is affixed externally to the patient adjacent to the hip joint implant. Preferably, the position sensors are used to properly orient the femur head and the acetabulum during implant surgery and to confirm that the proper orientation is maintained during the post-surgical period.

In another preferred embodiment, the medical device comprises an artificial knee. The signal processor, as described hereinabove, is adapted to determine the relative positions of the articulating portions of the artificial knee responsive to the output signals from the position sensors. Preferably, the energy transfer amplifier is implanted in or placed near the artificial knee, in close proximity to the position sensors. The position information thus generated is used to properly place the artificial knee during surgery and to monitor the knee post-operatively.

In some further preferred embodiments of the present invention, the energy transfer amplifier is used to improve the wireless transfer of power to implantable physiologic monitors. In a preferred embodiment, an implantable cardiac monitor is used to track the functioning of a patient's heart and report to a physician via continuous or periodic downloads of data to an external analysis device, such as a computer. The energy transfer amplifier is used to improve the wireless transfer of energy to the implanted device such that more power is available to transmit the data to the analysis device. The improved energy transfer can be used in the immediate transfer of data and/or to charge energy storage devices such as batteries or capacitors. Alternative physiologic monitors comprise: blood flow monitors, blood oxygenation monitors, and blood insulin level monitors.

In additional preferred embodiments of the present invention, the energy transfer amplifier is used to improve the wireless transfer of power to position sensors incorporated into invasive probes, such as catheters that are used for mapping of electrical activity in a heart. In a preferred embodiment of the present invention, the energy transfer amplifier is positioned on skin of a subject in a vicinity of the heart to improve the wireless transfer of energy to one or more position sensors incorporated into a catheter that has been inserted into the heart. Alternatively, the energy transfer amplifier is placed within the subject's body, for example by being fixed to the catheter, or by being temporarily placed within a chamber of the subject's heart.

In still further preferred embodiments of the present invention, the energy transfer amplifier is used to improve the wireless transfer of power to implantable electrical stimulation devices. In a preferred embodiment of the present invention, the energy transfer amplifier is implanted adjacent to a cardiac pacemaker to improve the wireless transfer of energy to the pacemaker, so as to charge the power source of the pacemaker. Additional embodiments of the present invention comprise using the energy transfer amplifier to improve the wireless transfer of energy to implantable devices for stimulating the brain or the pancreas.

There is therefore provided, in accordance with an embodiment of the present invention, apparatus for driving current in a power circuit of a medical device inserted into a body of a subject, the apparatus including:

a power transmitter, which is adapted to generate, in a vicinity of the body, an electromagnetic field having a predetermined frequency capable of inductively driving the current in the power circuit; and a passive energy transfer amplifier, having a resonant response at the frequency of the electromagnetic field and adapted to be placed in proximity to the medical device so as to enhance the current driven in the power circuit by the electromagnetic field.

Typically, the passive energy transfer amplifier includes a coil and a capacitance, which are coupled so as to define a resonant circuit having the resonant response at the frequency of the electromagnetic field.

There is also provided, in accordance with an embodiment of the present invention, apparatus for use in an invasive medical procedure, including:

a wireless medical device, which is adapted to be inserted into a body of a subject, the device including a power circuit, which is adapted to be driven inductively by a radio-frequency (RF) electromagnetic field so as to provide operating energy to the device;

a power transmitter, which is adapted to generate the RF electromagnetic field in a vicinity of the body; and a passive energy transfer amplifier, which is adapted to be placed in proximity to the medical device so as to enhance inductive driving of the power circuit of the wireless medical device by the RF electromagnetic field.

In some embodiments, the passive energy transfer amplifier is adapted to be implanted in the body in proximity to the medical device. In other embodiments, the passive energy transfer amplifier is adapted to be fixed externally to the body in proximity to an area of the body into which the medical device is inserted.

In some embodiments, the medical device includes a sensor, which is adapted to sense a parameter within the body, and a signal transmitter, which is coupled to transmit a signal indicative of the parameter to a receiver outside the body. In one embodiment, the power circuit of the wireless medical device includes a coil antenna for receiving the electromagnetic field, and the signal transmitter is coupled to transmit the signal via the coil antenna. Typically, the sensor includes a position sensor, and the transmitted signal is indicative of position coordinates of the medical device within the body. In one embodiment, the position sensor includes a sensor coil, and the apparatus further includes one or more field generators, which are adapted to generate energy fields in a vicinity of the medical device, which cause currents to flow in the sensor coil responsively to the position coordinates of the medical device.

In another embodiment, the parameter that is sensed by the sensor includes a physiological parameter. Typically, the physiological parameter includes an electrical parameter or, alternatively or additionally, at least one of a temperature, a pressure, a chemical parameter and a flow parameter.

In a further embodiment, the medical device is adapted to apply at least a portion of the operating energy to tissue in the body. Typically, the medical device includes an electrode, which is adapted to apply electrical energy to the tissue.

There is additionally provided, in accordance with an embodiment of the present invention, apparatus for use in an invasive medical procedure, including:

a wireless medical device, which is adapted to be inserted into a body of a subject, the device including a power circuit, which is adapted to be driven inductively by a radio-frequency (RF) electromagnetic field generated by a power transmitter outside the body, so as to provide operating energy to the device; and a passive energy transfer amplifier, which is adapted to be placed in proximity to the medical device so as to enhance inductive driving of the power circuit of the wireless medical device by the RF electromagnetic field.

There is further provided, in accordance with an embodiment of the present invention, an orthopedic implant, including:

a prosthetic joint including first and second joint elements, which are adapted to be implanted in a body of a subject;

first and second wireless position sensors, which are respectively fixed to the first and second joint elements so as to transmit position signals indicative of an alignment of the first and second joint elements, each of the position sensors including a power circuit, which is adapted to be driven inductively by a radio-frequency (RF) electromagnetic field so as to provide operating energy to the sensors;

a power transmitter, which is adapted to generate the RF electromagnetic field in a vicinity of the body; and a passive energy transfer amplifier, which is fixed to at least one of the first and second joint elements so as to enhance inductive driving of the power circuit of the wireless position sensors by the RF electromagnetic field.

In one embodiment, the prosthetic joint includes a hip joint, and the first and second joint elements include a femur head element and an acetabulum element, and the passive energy transfer amplifier is fixed to the acetabulum element. In another embodiment, the prosthetic joint includes a knee joint.

There is moreover provided, in accordance with an embodiment of the present invention, invasive medical apparatus, including:

a catheter, having a distal end, which is adapted to be inserted into a heart of a subject, the catheter including a wireless position sensor, fixed adjacent to the distal end of the catheter so as to transmit position signals indicative of a position of the catheter within the heart, the position sensor including a power circuit, which is adapted to be driven inductively by a radio-frequency (RF) electromagnetic field so as to provide operating energy to the position sensor;

a power transmitter, which is adapted to generate the RF electromagnetic field in a vicinity of the body; and a passive energy transfer amplifier, which is adapted to be placed in a vicinity of the heart so as to enhance inductive driving of the power circuit of the wireless position sensors by the RF electromagnetic field.

Typically, the passive energy transfer amplifier is adapted to be placed on a chest of the subject adjacent to the heart.

In a disclosed embodiment, the wireless position sensor includes a sensor coil, and the apparatus further includes one or more field generators, which are adapted to generate energy fields in a vicinity of the heart, wherein the energy fields cause currents to flow in the sensor coil responsively to the position coordinates of the medical device.

Additionally or alternatively, the catheter further includes one or more electrodes for sensing electrical activity within the heart.

There is furthermore provided, in accordance with an embodiment of the present invention, a method for driving current in a power circuit of a medical device inserted into a body of a subject, the method including:

generating, in a vicinity of the body, an electromagnetic field having a predetermined frequency capable of inductively driving the current in the power circuit; and placing a passive energy transfer amplifier, having a resonant response at the frequency of the electromagnetic field, in proximity to the medical device so as to enhance the current driven in the power circuit by the electromagnetic field.

The present invention will be more fully understood from the following detailed description of the preferred embodiments thereof, taken together with the drawings, in which:

DETAILED DESCRIPTION OF PREFERRED EMBODIMENTS

Figure 1:
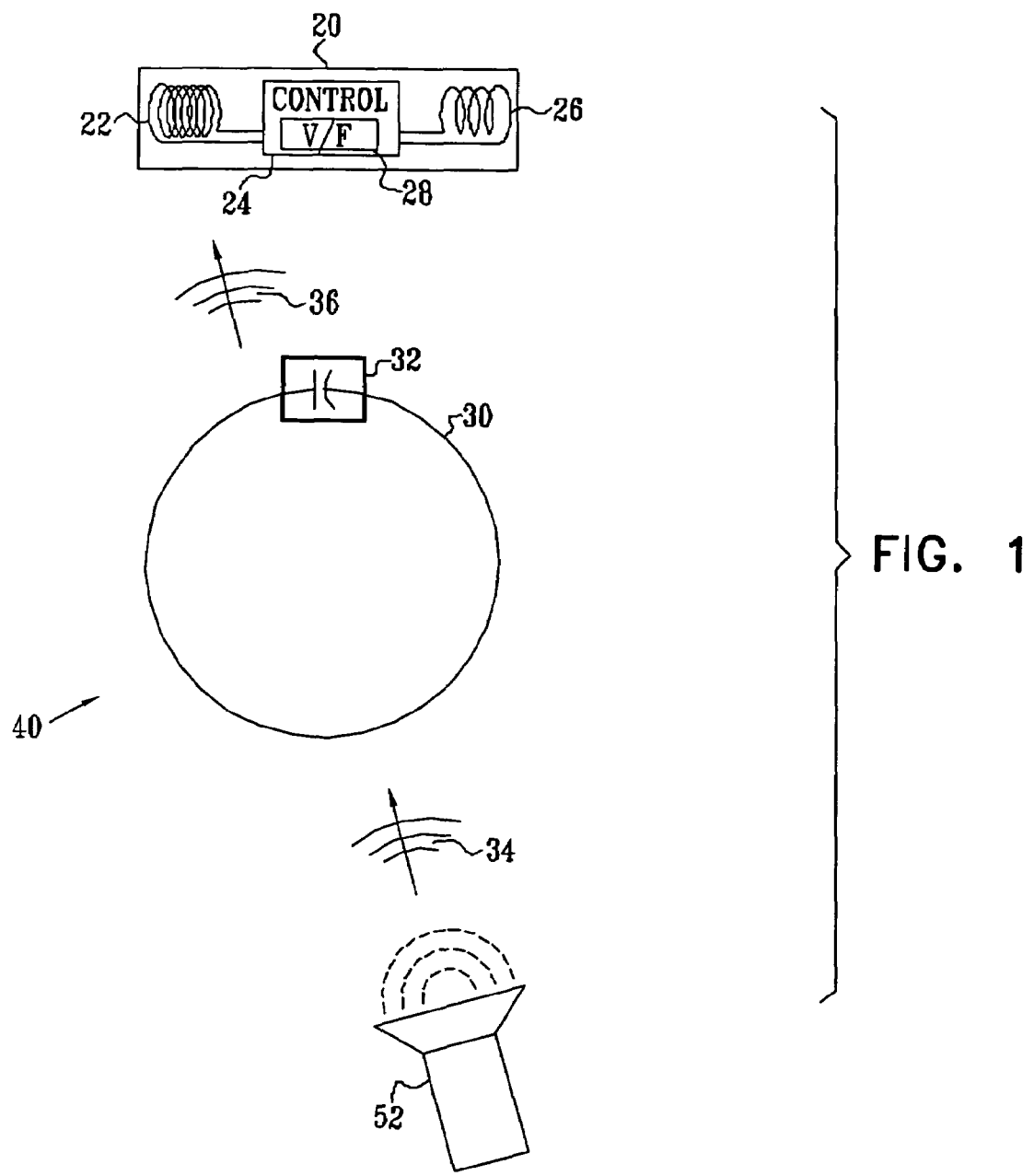
FIG. 1 is a schematic illustration showing details of a an energy transfer amplifier and a wireless location sensor, in accordance with a preferred embodiment of the present invention.

FIG. 1 (not to scale) is a schematic illustration of the interaction of an energy transfer amplifier 40 with a sensor 20, in accordance with a preferred embodiment of the present invention. Preferably, energy transfer amplifier 40 comprises at least one wire loop 30 and an inline capacitance 32, in series therewith. Capacitance 32 may comprise a discrete capacitor or, alternatively or additionally, an inherent capacitance provided by the structure of loop 30 and other elements of amplifier 40. Energy transfer amplifier 40 is used to enhance energy transfer to a sensor 20, which comprises a power coil 22. A power transmitting unit 52 produces a radio frequency (RF) electromagnetic field 34 that drives a current in both power coil 22 and energy transfer amplifier 40. Energy transfer amplifier 40, in turn, inductively drives power coil 22. Wire loop 30 preferably has a characteristic diameter substantially larger than that of power coil 22.

Preferably, inline capacitance 32 is chosen so that loop 30 and capacitance 32 form a resonant circuit, having a resonance at the frequency of electromagnetic field 34. This resonance increases the inductive driving of power coil 22, since it tends to generate a stronger field in the vicinity of loop 30 (and particularly along the axis of the loop) than would be generated by power transmitting unit 52 on its own. For example, electromagnetic field 34 may have a frequency of 13.6 MHz and capacitor 32 may be approximately 50 pF, so as to induce resonance in loop 30, and thereby drive loop 30 to also radiate at 13.6 MHz. Other combinations of electromagnetic field frequency and capacitor strength, chosen so as to cause resonance between transfer amplifier 40 and the electromagnetic field, are used in other preferred embodiments. The large size of coil 30 has been shown to increase the current in power coil 22 by at least 20 times, in experiments carried out by the inventor. Thus, the power available to drive sensor 20 is significantly increased.

In a preferred embodiment, the increased power available to sensor 20 is used to power circuitry such as a controller 24, which includes a voltage-to-frequency converter 28 to aid in transmitting measurements from a sensing coil 26 out of the sensor via the power induced in power coil 22. The extra power is also used to increase the signal strength of the outgoing sensor signal. For some applications, the increased power available provided by use of amplifier 40 permits the use of a lower-power electromagnetic field 34, which in turn generally reduces any interference in sensing coil 26 caused by magnetically-responsive articles in the vicinity of sensor 20.

In a preferred embodiment of the present invention, at least one sensor 20 is attached to or incorporated into a medical device for insertion into or implantation in a subject. For some applications, sensor 20 comprises a wireless position sensor. For other applications, sensor 20 comprises another type of sensor or active element, such as a sensing electrode, a temperature sensor, a chemical sensor, optical sensor or acoustic sensor. Alternatively or additionally, the medical device may comprise an active element, such as a pacing electrode, an ablation element, or an acoustic radiator, powered by coil 22.

Figure 2:
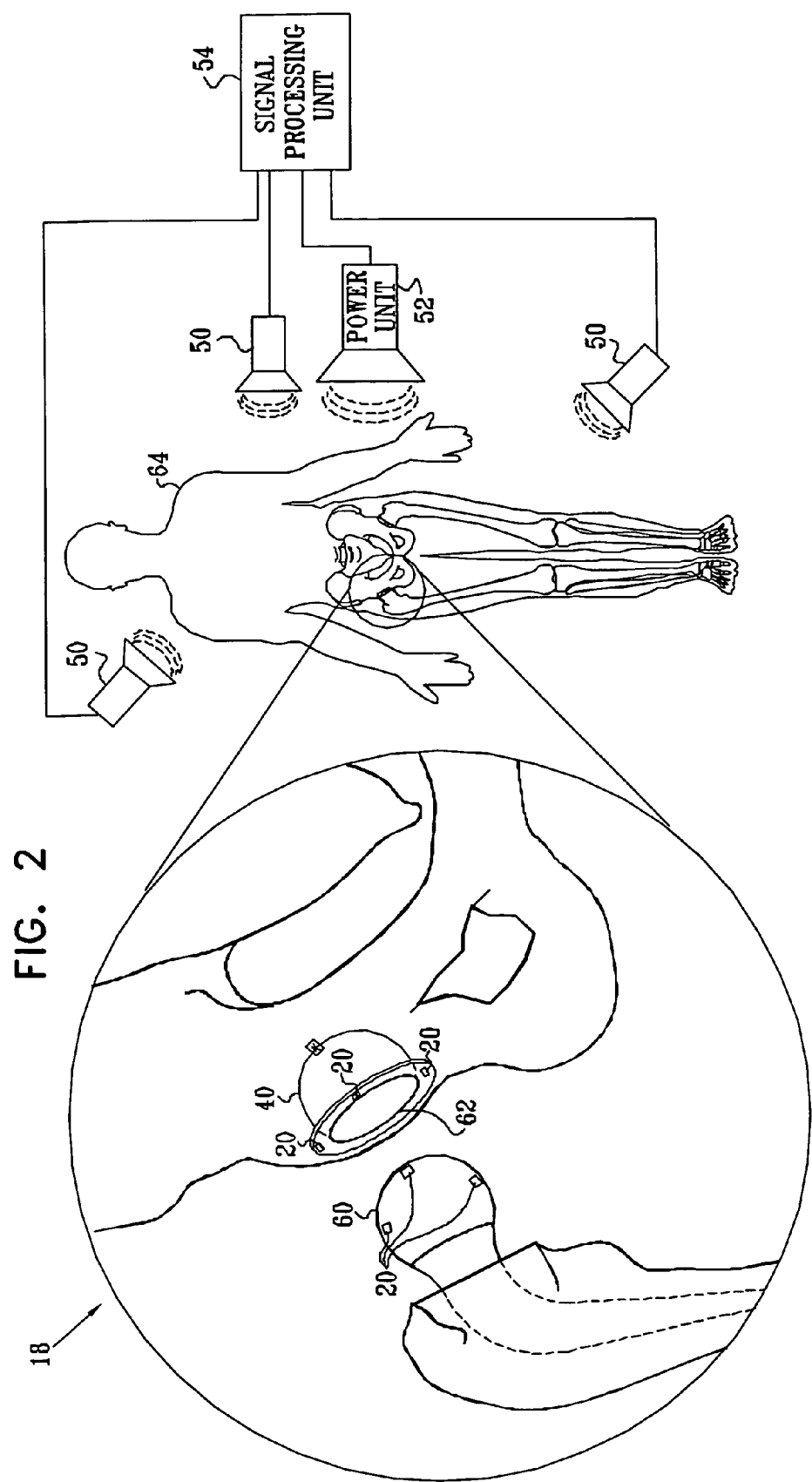
FIG. 2 is a schematic, pictorial illustration showing the use of the energy transfer amplifier and wireless location sensors of FIG. 1 in a joint implant, in accordance with a preferred embodiment of the present invention.

FIG. 2 is a schematic, pictorial illustration showing a position sensing system 18 for use in an orthopedic procedure, in accordance with a preferred embodiment of the present invention. In this preferred embodiment, position sensing during surgery is facilitated in a patient 64 who undergoes a hip replacement, in which an artificial femur 60 and an artificial acetabulum 62 are implanted.

It is considered beneficial during surgery to properly align the head of femur 60 in acetabulum 62 and to maintain proper alignment over time, in order to increase the working lifespan of the implant. To facilitate proper alignment of femur 60 and acetabulum 62, a plurality of wireless position sensors 20 are preferably incorporated within femur 60 and acetabulum 62. Preferably, wireless position sensors 20 are located so as to aid in the alignment and orientation between femur 60 and acetabulum 62 during surgery, and/or to facilitate post-surgical confirmation of proper placement.

Typically, but not necessarily, techniques described in U.S. patent application Ser. No. 10/029,473 to Govari, filed Dec. 21, 2001, entitled, "Wireless position sensor," which is assigned to the assignee of the present patent application and incorporated herein by reference, are adapted for use with the techniques of these embodiments of the present invention. In particular, as shown in FIG. 1, each position sensor 20 may comprise a wireless location transponder, comprising a power coil 22, a sensing coil 26, and a controller 24, as described in the '473 application. As shown in FIG. 2, at least one externally-located power transmitting unit 52 sends a radio frequency (RF) signal, preferably having a frequency in the megahertz range, to drive power coil 22 in the transponder and thereby power the chip. Additionally, a set of electromagnetic field generators 50 in fixed locations outside the body produce electromagnetic fields at different, respective frequencies, typically in the kilohertz range. These fields cause currents to flow in sensing coil 26, which depend on the spatial position and orientation of the sensing coil relative to the field generators. The processing chip converts these currents into high-frequency signals, which are transmitted by the power coil to an externally-located signal processing unit 54. This unit processes the signal in order to determine position and orientation coordinates of the object for display and recording. Position sensor 20 is preferably able to generate six position and orientation dimensions, using techniques described in the above-cited PCT Patent Publication to Ben-Haim et al., or other techniques known in the art. Although position sensor 20 is described hereinabove as comprising coils, position sensor 20 can also comprise field sensors other than coils, such as Hall effect devices or other antennae.

Preferably, wireless position sensors 20 are powered by an external 13.6 MHz electromagnetic field. The power transmitted to sensors 20 generally decays according to the cube of the distance between the source and the sensors, so there is typically a reduction in the power transmitted to the sensors responsive to the distance. Additionally, because the current induced in a coil varies linearly with the cross-sectional area of the coil, and, since position sensors 20 are relatively small (typically on the order of a few millimeters), the induced current in the power coils of the position sensors is significantly smaller than it would be if the power coils were larger, making it correspondingly more difficult to receive power at the sensors and/or to transmit signals from the sensor.

To increase the power transmitted to sensors 20, an energy transfer amplifier 40 is implanted adjacent to the sensors, preferably in acetabulum 62, such that it is in close proximity to the position sensors, so as to improve the wireless transfer of energy to the position sensors. Furthermore, in this case, since energy transfer amplifier 40 is completely enclosed by implanted acetabulum 62, no additional surgical procedure is necessary to implant the apparatus. Moreover, since the energy transfer amplifier is isolated from bodily tissues, biocompatibility issues are generally minimal. Energy transfer amplifier 40 is preferably substantially larger than sensors 20. While sensors 20 are typically a few millimeters in size, coils in energy transfer amplifier 40 are typically about 5 to 10 centimeters in diameter. Since induced current is generally proportional to the cross-sectional area of a coil, the induced current in the energy transfer amplifier is typically much larger than the induced current in a coil contained in a sensor, for a given electromagnetic field.

In a preferred embodiment of the present invention, position sensor 20 is attached to or incorporated in an artificial knee. Techniques generally similar to those described hereinabove with reference to FIG. 2 are preferably used. A signal processor is adapted to determine the relative positions of the two articulating portions of the artificial knee, responsive to the output signals from the position sensors. Preferably, the energy transfer amplifier is implanted in or placed near the artificial knee, in close proximity to the position sensors. The position information obtained in this manner is used to properly place the artificial knee during surgery and to monitor the knee post-operatively.

In another preferred embodiments of the present invention, the energy transfer amplifier is used to improve the wireless transfer of power to implantable physiologic monitors. In a preferred embodiment, an implantable cardiac monitor is used to track the functioning of a patient's heart and report to a physician via continuous or periodic downloads of data to an external analysis device, such as a computer. The energy transfer amplifier is used to improve the wireless transfer of energy to the implanted device such that more power is available to transmit the data to the analysis device. The improved energy transfer can be used in the immediate transfer of data and/or to charge energy storage devices such as batteries or capacitors. Alternative physiologic monitors include, but are not limited to, blood flow monitors, blood oxygenation monitors, and blood insulin level monitors.

Figure 3:
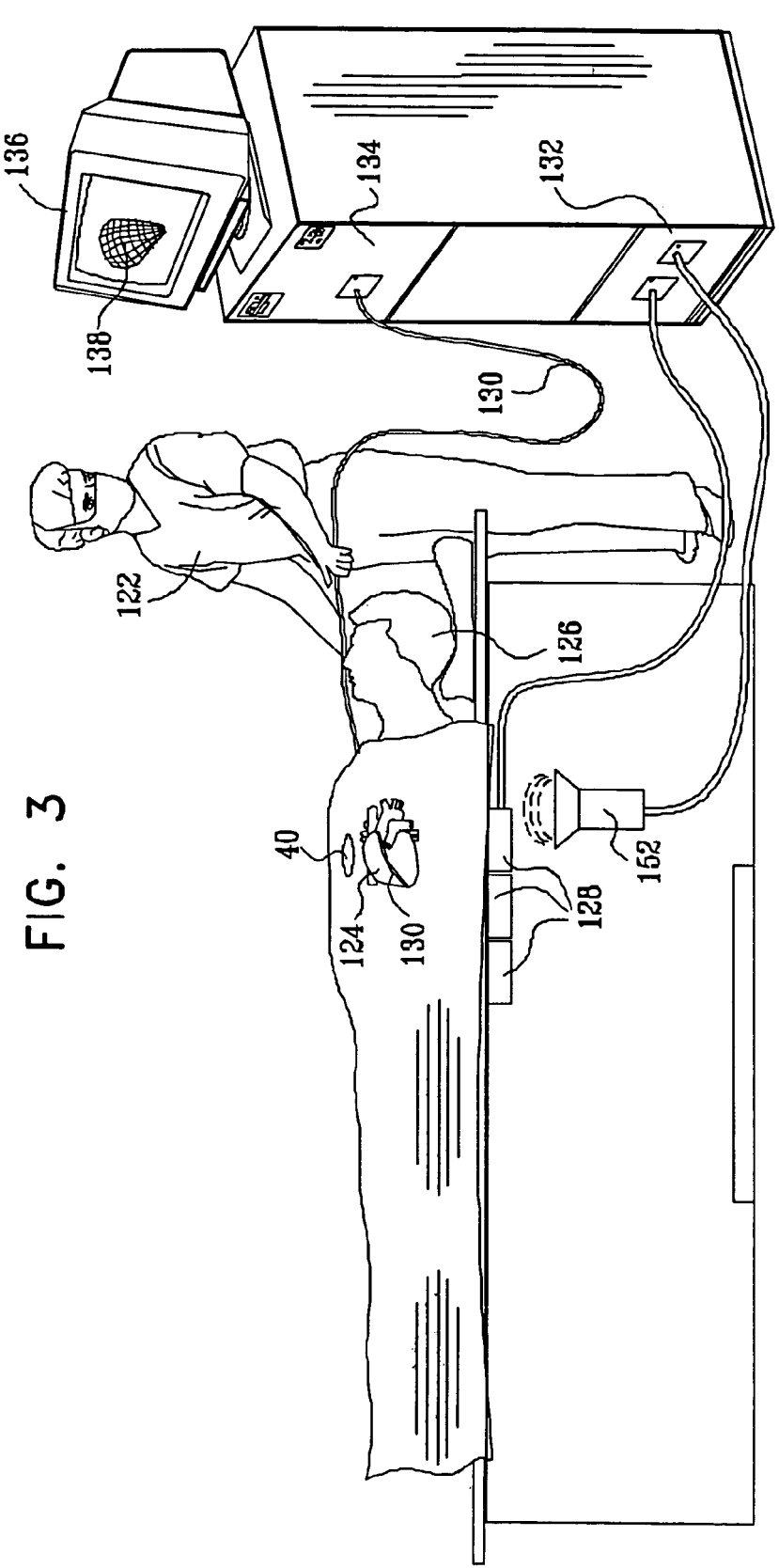
FIG. 3 is a schematic, pictorial illustration of a mapping system, for mapping of electrical activity in a heart, in accordance with a preferred embodiment of the present invention.
Figure 4:
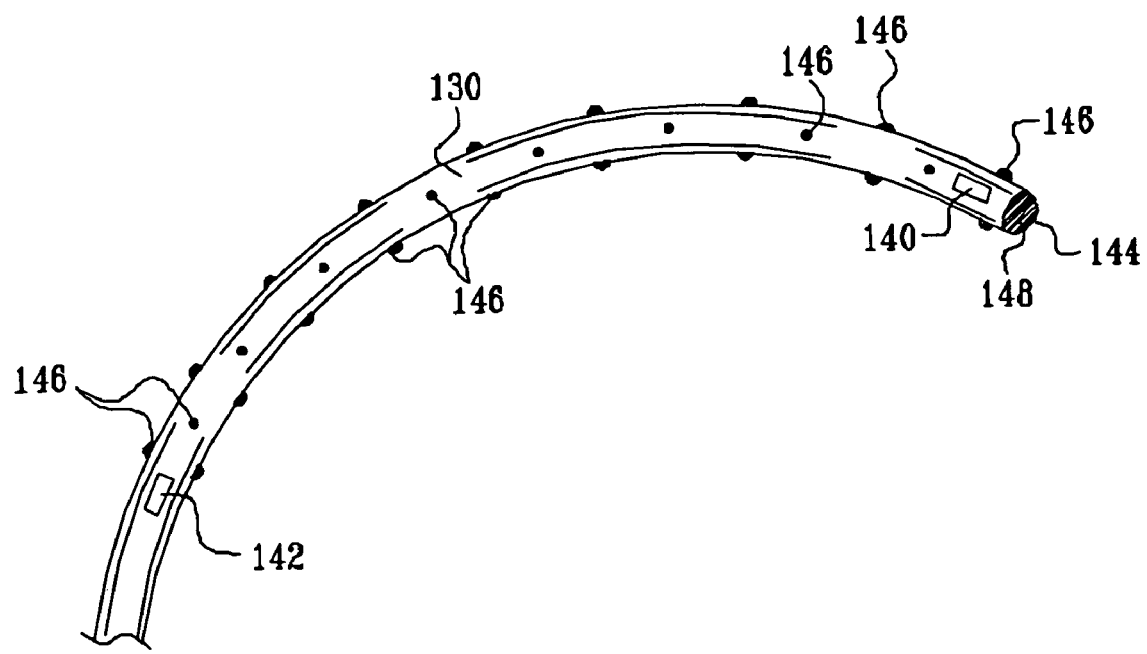
FIG. 4 is a schematic, pictorial illustration showing a distal portion of a catheter for use in the mapping system of FIG. 3, in accordance with a preferred embodiment of the present invention.

Reference is now made to FIGS. 3 and 4, which are schematic, pictorial illustration of a mapping system 120, for mapping of electrical activity in a heart 124 of a subject 126, and of a catheter 130 used in system 120, in accordance with a preferred embodiment of the present invention. Catheter 130 is inserted by a user 122 through a vein or artery of the subject into a chamber of the heart. The catheter has an array of shaft electrodes 146 on its outer surface, most preferably in a grid arrangement as shown in FIG. 4. Alternatively, the electrodes may comprise ring electrodes, or substantially any other suitable type of surface electrodes, as are known in the art. Additionally, the catheter optionally has one or more tip electrodes 148, typically at or near a distal tip 144 of the catheter.

For some applications, at least one of the electrodes also functions as an ablating electrode, for ablating cardiac tissue of the subject. Alternatively, at least one separate electrode is provided for this purpose (not shown).

Catheter 130 also comprises position sensors 140 and 142, preferably one of them near distal tip 144 and the other near a proximal end of the array of electrodes. The sensors preferably comprise wireless transponders, similar to sensors 20, as described hereinabove with reference to FIG. 1. The position sensors are fixed to or within catheter 130 by any suitable method, for example, using polyurethane glue or the like.

To use sensors 140 and 142, the patient is placed in an electromagnetic field generated, for example, by situating under the patient a pad containing field generator coils 128 for generating magnetic fields. These fields cause currents to flow in sensing coils 26, as described above. A reference electromagnetic sensor (not shown) is preferably fixed relative to the patient, e.g., taped to the patient's back, and catheter 130 containing sensors 140 and 142 is advanced into the patient's heart. The sensors are preferably powered by a power transmitting unit 152, which produces an electromagnetic field that drives a current in power coil 22 (FIG. 1) of sensors 140 and 142 (FIG. 4). Sensors 140 and 142 preferably transmit position signals using coil 22, which signals are received by field generator coils 128. These signals are amplified and transmitted to a computer housed in a console 34 (FIG. 3), in a form understandable to the computer. The computer analyzes the signals so as to determine and visually display the precise location of sensors 140 and 142 in the catheter relative to the reference sensor. The sensors can also detect displacement of that catheter that is caused by contraction of the heart muscle.

At least one passive energy transfer amplifier 40 is placed on or near subject 126, such as on skin of the subject near the heart. For example, amplifier 40 may be fixed to or within an adhesive patch, which is stuck onto the subject's chest in the proper location. The electromagnetic field produced by power transmitting unit 152 to power sensors 140 and 142 also drives a current in amplification coil 30 of the energy transfer amplifier (FIG. 1), which, in turn, inductively drives power coil 22 in sensors 140 and 142. Wire loop 30 preferably has a characteristic diameter substantially larger than that of power coil 22. Thus, energy transfer amplifier 40 enhances energy transfer to the sensors from power transmitting unit 152.

Some of the features of catheter 130 and system 120 are implemented in the NOGA-STAR catheter marketed by Cordis Webster, Inc., and in the above-mentioned Biosense-NOGA system, also marketed by Cordis Webster, Inc. Further aspects of the design of catheter 130 and of system 120 generally are described in U.S. patent application Ser. No. 09/506,766, which is assigned to the assignee of the present application and is incorporated herein by reference.

As noted above, sensors 140 and 142 each comprise one or more sensing coils 26, which act as AC magnetic field receivers, to sense the AC magnetic fields generated by field generator coils 128 (which are also referred to as magnetic field transmitters or radiators). Coils 128 generate AC magnetic fields to define a fixed frame of reference. Preferred implementations of sensing coils 26 and of position sensors based on such coils are further described in the above-mentioned U.S. Pat. No. 5,391,199 and PCT publication WO 96/96/05768. The position and orientation coordinates of the distal portion of catheter 130 are ascertained by determining the position and orientation of sensors 140 and 142 (through identifying the position and orientation coordinates thereof) relative to coils 128. Sensors 140 and 142 may each comprise a single sensing coil 26, as shown in FIG. 1, or may alternatively comprise two, three or more sensor coils, wound on either air cores or a core of material.

In a preferred embodiment of the invention (not shown in the figures), the sensor coils have mutually orthogonal axes, one of which is conveniently aligned with the long longitudinal axis of catheter 130. Unlike prior art position sensors (used for other applications), which contain three coils that are concentrically located, or at least whose axes intercept, the sensor coils in the present embodiment are closely spaced along the longitudinal axis of catheter 130 to reduce the diameter of sensors 140 and 142 and thus make the sensors suitable for incorporation into catheter 130 (which may also contain a lumen as a working channel within the catheter).

It should be understood that placement of field generator coils 128, as well as their size and shape, will vary according to the application of the invention. Preferably, in system 120, coils 128 comprise wound annular coils from about 2 to 20 cm in outer diameter (O.D.) and from about 0.5 to 2 cm thick, in a coplanar, triangular arrangement wherein the centers of the coils are from about 2 to 30 cm apart. Bar-shaped transmitters or even triangular or square-shaped coils could also be useful for such medical applications. Moreover, in instances where subject 126 is prone, as shown in FIG. 3, field generators 128 are preferably positioned in or below the surface upon which the subject is resting (such as an operating table), substantially directly below the portion of the subject's body 90 where the procedure is being performed.

Field generator coils 128 are driven by a radiator driver 132. The position signals transmitted by sensors 140 and 142 in response to the fields of coils 128 are received by coils 128 or by another receiving antenna. These signals are amplified and processed, together with a representation of the signals used to drive transmitters coils 128, preferably in the manner described below, by a console 134. The console provides a display or other indication of the position and orientation of the distal end of catheter 130 on a monitor 136.

Field generator coils 128 may be arranged in any convenient position and orientation, so long as they are fixed in respect to some reference frame, and so long as the coils are non-overlapping (i.e., there are no two coils 128 with the same position and orientation). When driven by radiator driver 132, coils 128 generate a multiplicity of distinguishable AC magnetic fields that form the magnetic field sensed by sensing coils 126 in the sensors 140 and 142. The magnetic fields are distinguishable with regard to the frequency, phase, or both frequency and phase of the signals in the respective magnetic fields. Time multiplexing is also possible.

In a preferred embodiment of the invention, sensors 140 and 142 in system 120 are used to determine six position and orientation coordinates (X, Y, Z directions and pitch, yaw and roll orientations) of the distal end and distal tip of catheter 130. For this purpose, at least two sensing coils are typically required in the location sensors. Preferably, three sensing coils are used, as described above, to improve the accuracy and reliability of the position measurement. Alternatively, if only a single sensing coil 26 is used in each sensor, the system 130 may be able to determine only five position and orientation coordinates (X, Y, Z directions and pitch and yaw orientations). Specific features and functions of a position tracking system with a single sensing coil (also referred to as a single axis system) are described in commonly-assigned U.S. Pat. No. 6,484,118, which is incorporated herein by reference.

In one embodiment of the invention, each sensing coil 26 has an inner diameter of 0.5 mm and comprises 800 turns of 16 μm diameter to give an overall coil diameter of 1-1.2 mm. The effective capture area of the sensing coil in this case is preferably about 400 mm². It will be understood that these dimensions may vary over a considerable range and are only representative of a typical range in certain embodiments. In particular, the size of the sensing coils can be as small as 0.3 mm (with some loss of sensitivity) and as large as 2 or more mm. In other embodiments, the wire size of the sensing coils can range from 10 to 31 μm, and the number of turns between 300 and 2600, depending on the maximum allowable size and the wire diameter. The effective capture area may advantageously be made as large as feasible, consistent with the overall size requirements.

While the preferred sensing coil shape is cylindrical, other shapes can also be used. For example a barrel shaped coil can have more turns than a cylindrical shaped coil for the same diameter of catheter. Also, square or other shaped coils may be useful depending on the geometry of catheter 130. Location sensors 140 and 142 may be used to determine both when the catheter is in contact with the tissue of heart 124 and also when the heart is not in motion. During diastole, the heart is relatively motionless for a short period of time (at most, a few hundred milliseconds). In addition to using location sensors 140 and 142, the location of catheter 130 may be determined using outside sensing or imaging means.

As noted above, catheter 130 is coupled to console 134, which enables the user to observe and regulate the functions of the catheter. Console 134 includes a processor, preferably a computer with appropriate signal processing circuits (which are typically contained inside a housing of the computer). The processor is coupled to drive monitor 136. The signal processing circuits typically receive, amplify, filter and digitize signals from catheter 130, including signals generated by position sensors 140 and 142 and electrodes 146 that are amplified by energy transfer amplifier 40. The digitized signals are received and used by the console to compute the position and orientation of the catheter and to analyze the electrical signals from the electrodes. The information derived from this analysis is preferably used to generate a map 138 of the heart's electrical activity.

Typically, system 120 includes other elements, which are not shown in the figures for the sake of simplicity. Some of these elements are described in U.S. Pat. No. 6,226,542 to Reisfeld, which is assigned to the assignee of the present patent application and is incorporated herein by reference. For example, system 120 may include an ECG monitor, coupled to receive signals from one or more body surface electrodes, so as to provide an ECG synchronization signal to console 134. As mentioned above, the system typically also includes a reference position sensor, either on an externally-applied reference patch attached to the exterior of the patient's body, or on an internally-placed catheter, which is inserted into heart 124 and maintained in a fixed position relative to the heart. By comparing the position of catheter 130 to that of the reference catheter, the coordinates of catheter 130 are accurately determined relative to the heart, irrespective of heart motion. Alternatively, any other suitable method may be used to compensate for heart motion.

As mentioned above, the information generated by catheter 130, facilitated by the operation of energy transfer amplifier 40, is used to generate a map of electrical activity over an endocardial surface of the chamber. For some applications, methods described in U.S. Pat. Nos. 6,226,542 and 6,301,496 to Reisfeld, which are assigned to the assignee of the present patent application and are incorporated herein by reference, are used to generate the map. As indicated in these patents, location and electrical activity is preferably initially measured on about 10 to about 20 points on the interior surface of the heart. These data points are then generally sufficient to generate a preliminary reconstruction or map of the cardiac surface to a satisfactory quality. The preliminary map is often combined with data taken at additional points in order to generate a more comprehensive map of the heart's electrical activity. In clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, which alters the propagation of the heart's electrical activity and restores normal heart rhythm.

Alternatively or additionally, methods described in U.S. Pat. Nos. 5,391,199 and 6,285,898 to Ben-Haim, U.S. Pat. Nos. 6,368,285 and 6,385,476 to Osadchy et al., and/or in U.S. Pat. No. 6,400,981, to Govari. All these patents are assigned to the assignee of the present patent application and are incorporated herein by reference, are used. Further alternatively or additionally, other methods known in the art for mapping the heart are used.

In a preferred embodiment of the present invention, the energy transfer amplifier is used to improve the wireless transfer of power to implantable electrical stimulation devices. In a preferred embodiment, the energy transfer amplifier is implanted adjacent to a cardiac pacemaker to improve the wireless transfer of energy to the pacemaker, so as to charge the power source of the pacemaker. Additional embodiments of the present invention comprise using the energy transfer amplifier to improve the wireless transfer of energy to implantable devices for stimulating the brain or the pancreas.

It will thus be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. Apparatus for use in an invasive medical procedure, comprising:
   a wireless position sensor, which is adapted to be inserted into a body of a subject, the position sensor comprising a power circuit, which is adapted to be driven inductively by a radio-frequency (RF) electromagnetic field so as to provide operating energy to the position sensor;
   a power transmitter, which is adapted to generate the RF electromagnetic field in a vicinity of the body; and
   a passive energy transfer amplifier, which is adapted to be placed in proximity to the position sensor so as to enhance inductive driving of the power circuit of the wireless position sensor by the RF electromagnetic field, the position sensor transmitting signals for determining six position and orientation coordinates of the position sensor; and
   a signal processing unit for receiving signals from the position sensor and determining six position and orientation coordinates of the position sensor.

2. The apparatus according to claim 1, wherein the power transmitter is adapted to generate the RF electromagnetic field at a predetermined frequency, and wherein the passive energy transfer amplifier has a resonant response at the predetermined frequency.

3. The apparatus according to claim 2, wherein the passive energy transfer amplifier comprises a coil and a capacitance, which are coupled so as to define a resonant circuit having the resonant response at the predetermined frequency.

4. The apparatus according to claim 1, wherein the passive energy transfer amplifier is adapted to be implanted in the body in proximity to the wireless position sensor.

5. The apparatus according to claim 4, wherein the wireless position sensor is for use in association with an orthopedic implant, and wherein the passive energy transfer amplifier is incorporated in the orthopedic implant.

6. The apparatus according to claim 5, wherein the implant is a hip joint implant, including a femur head element and an acetabulum element, and wherein the passive energy transfer amplifier comprises a coil, which is integrated in the acetabulum element.

7. The apparatus according to claim 1, wherein the passive energy transfer amplifier is adapted to be fixed externally to the body in proximity to an area of the body into which the wireless position sensor is inserted.

8. The apparatus according to claim 7, wherein the wireless position sensor is fixed to an invasive probe for insertion into a head of the subject, and wherein the passive energy transfer amplifier is adapted to be fixed to a chest of the subject.

9. The apparatus according to claim 8, wherein the wireless position sensor is adapted to provide an indication of location of the probe within the heart.

10. The apparatus according to claim 1, wherein the power circuit of the wireless position sensor comprises a coil antenna for receiving the electromagnetic field, and wherein the signal transmitter is coupled to transmit the signal via the coil antenna.

11. The apparatus according to claim 1, wherein the position sensor comprises a sensor coil, and wherein the apparatus further comprises one or more field generators, which are adapted to generate energy fields in a vicinity of the medical device, which cause currents to flow in the sensor coil responsively to the position and orientation coordinates of the wireless position sensor.

12. Apparatus for use in an invasive medical procedure, comprising;
a wireless position sensor, which is adapted to be inserted into a body of a subject, the device comprising a power circuit, which is adapted to be driven inductively by a radio-frequency (RF) electromagnetic field generated by a power transmitter outside the body, so as to provide operating energy to the wireless position sensor; and
a passive energy transfer amplifier, which is adapted to be placed in proximity to the wireless position sensor so as to enhance inductive driving of the power circuit of the wireless position sensor by the RF electromagnetic field, the wireless position sensor transmitting signals for determining six position and orientation coordinates of the position sensor; and
a signal processing unit for receiving signals from the position sensor and determining six position and orientation coordinates of the position sensor.

13. An orthopedic implant, comprising:
a prosthetic joint comprising first and second joint elements, which are adapted to be implanted in a body of a subject;
first and second wireless position sensors, which are respectively fixed to the first and second joint elements so as to transmit position signals indicative of an alignment of the first and second joint elements, each of the position sensors comprising a power circuit, which is adapted to be driven inductively by a radio-frequency (RF) electromagnetic field so as to provide operating energy to the sensors;
a power transmitter, which is adapted to generate the RF electromagnetic field in a vicinity of the body; and
a passive energy transfer amplifier, which is fixed to at least one of the first and second joint elements so as to enhance inductive driving of the power circuit of the wireless position sensors by the RF electromagnetic field; and
a signal processing unit for receiving the position signals and determining six position and orientation coordinates for the first and second wireless position sensor.

14. The implant according to claim 13, wherein the prosthetic joint comprises a hip joint, and wherein the first and second joint elements comprise a femur head element and an acetabulum element, and wherein the passive energy transfer amplifier is fixed to the acetabulum element.

15. The implant according to claim 13, wherein the prosthetic joint comprises a knee joint.

16. Invasive medical apparatus, comprising:
a catheter, having a distal end, which is adapted to be inserted into a heart of a subject, the catheter comprising a wireless position sensor, fixed adjacent to the distal end of the catheter so as to transmit position signals indicative of a position of the catheter within the heart, the position sensor comprising a power circuit, which is adapted to be driven inductively by a radio-frequency (RF) electromagnetic field so as to provide operating energy to the position sensor; a power transmitter, which is adapted to generate the RF electromagnetic field in a vicinity of the body; and
a passive energy transfer amplifier, which is adapted to be placed in a vicinity of the heart so as to enhance inductive driving of the power circuit of the wireless position sensors by the RF electromagnetic field; and
a signal processing unit for receiving the position signals and determining six position and orientation coordinates for the wireless position sensor.

17. The apparatus according to claim 16, wherein the passive energy transfer amplifier is adapted to be placed on a chest of the subject adjacent to the heart.

18. The apparatus according to claim 16, wherein the wireless position sensor comprises a sensor coil, and wherein the apparatus further comprises one or more field generators, which are adapted to generate energy fields in a vicinity of the heart, wherein the energy fields cause currents to flow in the sensor coil responsively to the position coordinates of the medical device.

19. The apparatus according to claim 16, wherein the catheter further comprises one or more electrodes for sensing electrical activity within the heart.

* * * * *

UNITED STATES PATENT AND TRADEMARK OFFICE
CERTIFICATE OF CORRECTION

PATENT NO. : 7,613,497 B2  Page 1 of 1
APPLICATION NO. : 10/629660
DATED : November 3, 2009
INVENTOR(S) : Assaf Govari and Michael Levin It is certified that error appears in the above-identified patent and that said Letters Patent is hereby corrected as shown below:

Column 15, Line 19 delete "head" and insert --heart--

Signed and Sealed this

Twenty-first Day of December, 2010

David J. Kappos
*Director of the United States Patent and Trademark Office*